United States Patent [19]

Dunbar

[11] 4,147,723

[45] Apr. 3, 1978

[54] 2-(MERCAPTO)-N,N'-p-PHENYLENEBIS-SULFONAMIDES

[75] Inventor: Joseph E. Dunbar, Midland, Mich.

[73] Assignee: The Dow Chemical Company, Midland, Mich.

[21] Appl. No.: 888,891

[22] Filed: Mar. 22, 1978

Related U.S. Application Data

[62] Division of Ser. No. 829,755, Sep. 1, 1977, Pat. No. 4,098,889.

[51] Int. Cl.$^2$ .................. C07C 143/75; C07C 143/79
[52] U.S. Cl. ...................... 260/556 A; 260/397.7 DS; 260/556B; 260/556 S
[58] Field of Search ............ 260/556 A, 556 B, 556 S, 260/397.7 DS

[56] References Cited

U.S. PATENT DOCUMENTS 3,067,237  12/1962  Larsen ........................ 260/556 A X
3,375,275  3/1968  Dunbar ........................... 260/556 A

FOREIGN PATENT DOCUMENTS 40-20542  9/1965  Japan .................................. 260/556 S Primary Examiner—Thomas Waltz
Attorney, Agent, or Firm—James W. Ambrosius

[57] ABSTRACT

Novel antithrombotic 2-(aminoalkylthio)-N,N'-p-phenylenebissulfonamides, a method for inhibiting blood platelet aggregation, and pharmaceutical compositions.

4 Claims, No Drawings

2-(MERCAPTO)-N,N'-P-PHENYLENEBISSULFONAMIDES

CROSS REFERENCE TO RELATED APPLICATION

This is a division of application Ser. No. 829,755 Filed Sept. 1, 1977, now U.S. Pat. No. 4,098,889.

BACKGROUND OF THE INVENTION

Adenosine diphosphate, hereafter called ADP, is a principal factor in the aggregation of blood platelets. Platelet aggregation in the blood stream of a mammal can lead to the formation of a thrombus. Agents which interfere with ADP-induced platelet aggregation are of use as antithrombotic drugs.

SUMMARY OF THE INVENTION

The present invention relates to novel 2-(aminoalkylthio)-N,N'-p-phenylenebissulfonamides, novel intermediates, pharmaceutical compositions, and methods of use for the inhibition of ADP-induced platelet aggregation. The compounds may be represented by the general formula

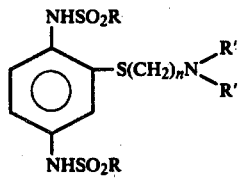

wherein n represents the integer 1, 2, or 3; R represents an alkyl having from 1 to about 3 carbon atoms or phenyl; and R' represents an alkyl having from 1 to about 4 carbon atoms or the two R' groups taken together with the adjacent nitrogen represent a 6-membered heterocyclic ring, as for example piperidinyl, and which may optionally contain an oxygen in the 4-position of the ring whereby morpholinyl residue is formed.

Compounds represented by the above general formula have been found to be effective in the inhibition of blood platelet aggregation and are useful as antithrombotic drugs in mammals.

The invention also includes the pharmaceutically-acceptable salts of the 2-(aminoalkylthio)-N,N'-p-phenylbissulfonamides described herein. As used in the specification and claims, the term "pharmaceutically-acceptable salts" refers to non-toxic acid addition salts of the compounds, the anions of which are relatively innocuous to animals at dosages consistent with good platelet aggregation inhibition so that the beneficial effects of the free base are not vitiated by the side effects ascribable to the anions. Pharmaceutically-acceptable salts include those derived from mineral acids such as hydrochloric and sulfuric acids and from organic acids such as lactic, maleic, succinic, fumaric, glutaric, citric, malic, p-toluenesulfonic, methanesulfonic and tartaric acids, and the like.

In general, the compounds of the present invention may be administered in daily dosages of from about 5.6 micromoles to about 400 micromoles of active ingredient per kilogram of body weight as platelet aggregation inhibiting agents. The compounds are administered internally to a mammal either orally or parenterally by subcutaneous, intravenous or intraperitoneal injection or the like, or by implantation or the like, oral administration being preferred. The effective blood platelet aggregation inhibiting amount of the compounds of the invention to be administered internally to a mammal, that is the amount which is effective to substantially inhibit the aggregation of blood platelets, can vary depending upon such factors as the animal treated, the particular compound administered, the period of administration, and the method of administration.

DETAILED DESCRIPTION OF THE INVENTION

Compounds falling within the scope of the present invention may be prepared using one of two methods. The first method is illustrated in Example 1 below. In general, compounds are synthesized by this method through the 1,4-addition of an aminoalkylthiol to a quinoneimide. In situations where the simple 1,4-addition is unsatisfactory due to competing side reactions, the second method as illustrated in Examples 2 and 3 may be used. In the second method, a 2-xanthyl-N,N'-p-phenylenebissulfonamide is saponified to form a 2-mercapto-N,N'-p-phenylenebissulfonamide. The mercaptan is then alkylated by a selected aminoalkylhalide. The general reaction sequence may be represented as follows:

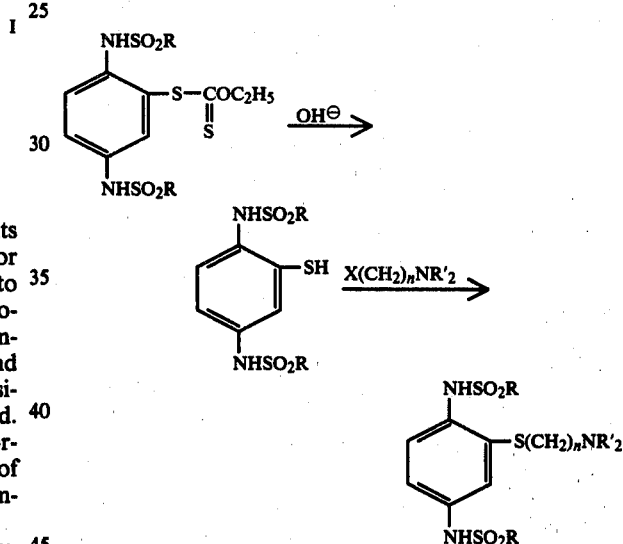

wherein X represents a halide and R, R', and n are as defined above.

In forming the compositions of the invention, the active ingredient is incorporated in a pharmaceutical carrier. The term "pharmaceutical carrier" refers to pharmaceutical excipients and includes nutritive compositions such as a solid or liquid foodstuff. In the present specification and claims, "pharmaceutical excipient" refers to known pharmaceutical excipients which are substantially non-toxic and non-sensitizing at dosages consistent with good platelet aggregation inhibiting activity. A preferred pharmaceutical carrier is a surface active dispersing agent.

Suitable solid pharmaceutical carriers which can be employed for formulating the compositions of the invention include starch, lactose, glucose, sucrose, gelatin, microcrystalline cellulose, powdered licorice, powdered tragacanth, malt, rice flour, silica gel, magesium stearate, magnesium carbonate, hydroxypropyl methyl cellulose, chalk and the like, and compatible mixtures thereof. In the preparation of solid compositions, the active ingredient can be triturated with a solid pharmaceutical carrier or mixtures thereof, or otherwise mechanically milled to obtain a uniform mixture. The mixtures can be compressed into tablets or filled into capsules by known procedures, or they can be employed as powders or the like. The solid compositions generally contain from about 0.02 to about 90, inclusive, percent by weight of the active ingredient.

Among the liquid pharmaceutical carriers which can be utilized are ethyl alcohol, propylene glycol, polyethylene glycols, peanut oil, corn oil, water, saline solution, glycerine and water mixtures, glucose syrup, syrup of acacia, mucilage of tragacanth and the like, and compatible mixtures thereof.

The compositions can also contain the active ingredient in admixture with surface-active dispersing agents and, optionally, an inert carrier. Suitable surface-active dispersing agents include natural phosphatides such as lecithin, natural gums such as gum acacia and gum tragacanth, condensation products of ethylene oxide with fatty acids, such as polyoxyethylene stearate, condensation products of ethylene oxide with fatty alcohols such as heptadecaethyleneoxycetanol and esters or partial esters of fatty acids with a hexitol or hexitol anhydride, and their condensation products with ethylene oxide, such as sorbitan monooleate, polyoxyethylene sorbitan monooleate and polyoxyethylene sorbitan monooleate. Such compositions can be in the form of emulsions, suspensions or dispersible powders or granules, and the compositions containing surface-active dispersing agents can also be in the form of tablets, capsules, or the like.

The pharmaceutical compositions described above can also contain, in addition, sweetening agents such as sugar, saccharin or the like, flavoring agents such as carmel, preservatives such as ethyl p-hydroxybenzoate, antioxidants such as ascorbic acid and suitable coloring materials.

The 2-(aminoalkylthio)-N,N'-p-phenylenebissulfonamide compounds can also be incorporated in a foodstuff such as, for example, butter, margarine, edible oils and the like. The active compounds can also be prepared in the form of a nutritive composition in which the active ingredient is mixed with vitamins, fats, proteins or carbohydrates and the like, or mixtures thereof. Such compositions can be prepared in liquid form such as emulsions or suspensions, as well as in solid form. The nutritive compositions are adapted to be administered as the total diet. The nutritive compositions preferably contain from 0.02 to about 2 percent of the active ingredient when administered as the total diet. The compositions can contain higher concentrations of the active ingredient when administered as a supplement.

The active ingredients can also be formulated as concentrated compositions which are adapted to be diluted by admixture with liquid or solid foodstuffs. The concentrated compositions are prepared by mechanically milling or otherwise mixing the active ingredient with an inert carrier such as silica gel, soluble casein, starch or the like, or mixtures thereof. The concentrated compositions can also include additional ingredients such as vitamins, preservatives, antioxidants and flavoring agents. Such compositions contain from 5 to about 90 percent of active ingredient.

The following examples serve to further illustrate the present invention but are not to be construed as a limitation thereon.

EXAMPLE 1

Preparation of 2-(2-(Diethylamino)ethylthio)-N,N'-p-phenylenebismethanesulfonamide Hydrochloride A solution containing 13.1 grams (0.05 mole) of p-quinonebismethanesulfonimide in 650 ml of acetone was treated with 8.5 grams (0.05 mole) of 2-(diethylamino)ethanethiol hydrochloride, two drops of triethylamine and one milliliter of water under stirring at a temperature of 45°C. The reaction mixture was allowed to stand at ambient temperature for 65 hours after which the solvent was removed by evaporation in vacuo. The crude product identified in the title remained as a gray solid. Two recrystallizations from nitromethane yielded while crystals of the title compound with a melting pint of 176°–176.5°C.

Elemental analysis showed carbon 39.1%, hydrogen 6.03% and nitrogen 9.87% as compared to calculated values of carbon 38.92%, hydrogen 6.07% and nitrogen 9.73%.

Other compounds falling within the scope of the present invention were also prepared using the simple 1,4-addition of an aminoalkylthiol to a quinoneimide as illustrated in Example 1. These compounds were as follows:

2-(2-(4-Morpholinyl)ethylthio)-N,N'-p-phenylenebismethanesulfonamide, m.p. 188°–189° C.

2-(2-Isopropylamino)ethylthio)-N,N'-p-phenylenebismethanesulfonamide, m.p. 73.5°–75.5° C.

2-(2-(Dimethylamino)ethylthio)-N,N'-p-phenylenebismethanesulfonamide, m.p. 162.5°–163.5° C.

Free bases as prepared above may be converted to the desired pharmaceutically-acceptable salt by simple acidification using a preselected acid as described above.

EXAMPLE 2

Preparation of 2-(2-(Diethylamino)ethylthio)-N,N'-p-phenylenebisbenzenesulfonamide Hydrochloride A solution containing 30.0 grams (0.06 mole) of 2-xanthyl-N,N'-p-phenylenebisbenzenesulfonamide and 250 ml of 10% aqueous sodium hydroxide was heated on a steam plate for about two and one half hours. The reaction mixture was cooled and acidified with 6N hydrochloric acid. The white precipitate that formed was collected on a filter and recrystallized wet from glacial acetic acid to give a pale yellow solid. The intermediate product, 2-mercapto-N,N'-p-phenylenebisbenzenesulfonamide, was recrystallized a second time from glacial acetic acid. The melting point was found to be 179.5°–181.5°C. Elemental analysis found carbon 51.4%, hydrogen 3.89%, and nitrogen 6.89% compared to calculated values of carbon 51.41%, hydrogen 3.84%, and nitrogen 6.66%.

A solution was prepared containing 4.21 grams (0.01 mole) of the mercaptan intermediate prepared above in 150 ml of absolute alcohol. While the resulting solution was stirred at 55°C., 1.50 grams (0.01 moles) of 2-(diethylamino)ethyl chloride was added. Following this addition, the reaction vessel was removed from the hotplate and with continued stirring was allowed to cool at ambient temperature over a period of about 30 minutes. The reaction mixture was cooled to about 5° to 10°C. in an ice bath. The title compound formed as a white crystalline solid and was filtered off, then dried. The product had a melting point of 188.5°–190° C.

Elemental analysis found carbon 52.09%, hydrogen 5.41% and nitrogen 7.61% as compared to calculated values of carbon 51.82% hydrogen 5.43% and nitrogen 7.56%.

EXAMPLE 3

Preparation of 2-(2-(1-Piperidinyl)ethylthio)-N,N'-p-phenylenebismethanesulfonamide Hydrochloride Potassium ethyl xanthate (19.3 grams, 0.120 mole) was added at room temperature to a stirred suspension of 26.2 grams (0.10 mole) of p-quinonedimethanesulfonimide in 500 ml of glacial acetic acid. After about ten minutes, the yellow color disappeared and the 2-xanthyl-N,N'-p-phenylenebismethanesulfonamide precipitated as a white solid. This was collected on a filter, washed with glacial acetic acid and then with ether, and finally dried in vacuo over potassium hydroxide. The xanthyl-intermediate was recrystallized from ethanol. Elemental analysis found carbon 34.2%, hydrogen 4.21% and nitrogen 7.12% as compared to calculated values of carbon 34.45%, hydrogen 4.20% and nitrogen 7.29%. The melting point was 174.5° C.

A solution of 68.6 g (0.178 mole) of 2-xanthyl-N,N'-p-phenylenebismethanesulfonamide in 430 ml of 10% aqueous sodium hydroxide was heated on the steam plate at 90°–95°C. for 50 minutes, poured into ice water and acidified with 6 N hydrochloric acid. The resulting white precipitate was dissolved in hot ethanol, and the solution treated with decolorizing charcoal. The hot mixture was filtered to remove the charcoal and the filtrate was allowed to cool, giving 46.0 g of the crude intermediate as a white solid, m.p. 169°–175° C. Recrystallization of the crude substance from water gave the pure intermediate 2-mercapto-N,N'-p-phenylenebismethanesulfonamide as a very pale yellow, crystalline solid, m.p. 174°–176° C.

Elemental analysis found carbon 32.4%, hydrogen 4.04% and nitrogen 9.55% as compared to calculated values of carbon 32.42%, hydrogen 4.08% and nitrogen 9.45%.

To a solution containing 8.9 g (0.030 mole) of 2-mercapto-N,N'-p-phenylenebismethanesulfonamide dissolved in 500 ml of ethanol at 60° C. was added 4.7 g (0.032 mole) of 2-(1-piperidinyl)ethyl chloride with stirring. The reaction flask was then removed from the heat, and the mixture was allowed to cool to room temperature. At the end of a period of 15 hours the precipitated white solid product (8.9 g) was collected on a filter and dried. Recrystallization from a mixture of nitromethane and dimethylformamide gave the title compound as white crystals, m.p. 218°–218.5° C. dec.

Elemental analysis found carbon 40.7%, hydrogen 5.86% and nitrogen 9.62% as compared to calculated values of carbon 40.57%, hydrogen 5.90% and nitrogen 9.46%.

EXAMPLE 4

Measurement of platelet aggregation in vivo was carried out using the technique described by Broersma et al., *Thomb. Diath. Haemorrhag.* 29, 201 (1973). Such determinations are based upon the measurement of the blood pressure proximal to a filter with 53 micron openings through which arterial blood flows. Platelet aggregation partially obstructs the filter with time causing a change in the pressure which is proportional to the degree of platelet aggregation (thrombosis).

Fasted male beagle dogs were anesthetized with sodium pentobarbital (35 mg/kg), heparinized (16.5 μ/kg, intravenous) and tested for platelet function using aggregometry. Compounds were administered orally in 0.5% Methocel$^{(R)}$ (Dow) solutions having the pH adjusted to about 7. Thrombus formation was observed using the filter occlusion technique outlined above. Platelet count, hemocrit, blood pressure, and heart rate were also measured.

Using the above techniques, the compound 2-(2-(dimethylamino)ethylthio)-N,N'-p-phenylenebismethanesulfonamide was found to reduce ADP-induced blood platelet aggregation by 60% in the dog at a dosage of 80 mg/kg of body weight. At the same dosage level, the compound 2-(2-(morpholinyl)ethylthio)-N,N'-p-phenylenebismethanesulfonamide hydrochloride reduced blood platelet aggregation by 43%. The compound 2-(2-(morpholinyl)ethylthio)-N,N'-p-phenylenebismethanesulfonamide reduced ADP-induced platelet aggregation by 42% at 40 mg/kg. The preferred compound was 2-(2-(diethylamino)ethylthio)-N,N'-p-phenylenebismethanesulfonamide hydrochloride which was found to reduce ADP-induced platelet aggregation by 45% at 20 mg/kg. The same compound was found to completely block collagen-induced platelet aggregation at 40 mg/kg.

The other compounds falling within the scope of the invention while generally less active than the preferred embodiments described above also displayed significant ADP-induced platelet aggregation inhibition.

I claim:
1. A compound of the formula

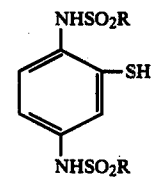

wherein R represents an alkyl having from 1 to about 3 carbon atoms or phenyl.

2. The compound of claim 1 wherein R is phenyl.
3. The compound of claim 11 wherein R is an alkyl of from 1 to about 3 carbon atoms.
4. The compound of claim 3 wherein R is methyl.

UNITED STATES PATENT AND TRADEMARK OFFICE
CERTIFICATE OF CORRECTION

PATENT NO. : 4,147,723
DATED : April 3, 1979
INVENTOR(S) : Joseph E. Dunbar

It is certified that error appears in the above-identified patent and that said Letters Patent are hereby corrected as shown below:

First page, under Patent No. 4,147,723, the issued date is "April 3, 1978", should read, --April 3, 1979--.

Column 4, line 16, "while" should read, --white--, and "pint" should read --point--.

Column 6, line 55, Claim 3, "Claim 11" should read, --Claim 1--.

Signed and Sealed this

*Second* Day of *October 1979*

[SEAL]

*Attest:*

RUTH C. MASON
*Attesting Officer*

LUTRELLE F. PARKER
*Acting Commissioner of Patents and Trademarks*